United States Patent [19]
Sahota

[11] Patent Number: 5,370,617
[45] Date of Patent: Dec. 6, 1994

[54] BLOOD PERFUSION BALLOON CATHETER

[76] Inventor: Harvinder Sahota, 3861 Wisteria, Seal Beach, Calif. 90740

[21] Appl. No.: 123,128

[22] Filed: Sep. 17, 1993

[51] Int. Cl.⁵ .............................................. A61M 29/00
[52] U.S. Cl. ...................................... 604/102; 604/53; 604/96; 606/194
[58] Field of Search ........................ 604/93, 95, 96, 97, 604/98, 99, 101, 102, 103, 104, 53; 606/191, 192, 194, 195

[56] References Cited

U.S. PATENT DOCUMENTS

| | | |
|---|---|---|
| 2,930,377 | 6/1958 | Cowley . |
| 3,045,677 | 5/1960 | Wallace . |
| 3,173,418 | 3/1965 | Baran . |
| 3,448,739 | 6/1969 | Stark et al. . |
| 3,889,686 | 6/1975 | Duturbure . |
| 4,029,104 | 6/1977 | Kerber . |
| 4,224,929 | 9/1980 | Furihata . |
| 4,233,983 | 11/1980 | Rocco . |
| 4,323,071 | 4/1982 | Simpson et al. . |
| 4,329,993 | 5/1982 | Lieber et al. . |
| 4,423,725 | 1/1984 | Baran et al. . |
| 4,445,892 | 5/1984 | Hussein . |
| 4,467,790 | 8/1984 | Schiff . |
| 4,547,193 | 10/1985 | Rydell . |
| 4,563,181 | 1/1986 | Wijayarathna et al. . |
| 4,564,014 | 1/1986 | Fogarty et al. . |
| 4,581,017 | 4/1986 | Sahota ................................... 604/96 |
| 4,608,984 | 9/1986 | Fogarty . |
| 4,644,936 | 2/1987 | Schiff . |
| 4,737,153 | 4/1988 | Shimamura et al. . |
| 4,744,366 | 5/1988 | Jang . |
| 4,762,129 | 8/1988 | Bonzel . |
| 4,763,654 | 8/1988 | Jang . |
| 4,784,639 | 11/1988 | Patel . |
| 4,785,815 | 11/1988 | Cohen . |
| 4,808,155 | 2/1989 | Mahurkar . |
| 4,822,345 | 4/1989 | Danforth . |
| 4,824,435 | 4/1989 | Giesy et al. . |
| 4,826,480 | 5/1989 | Diaz et al. . |
| 4,842,589 | 6/1989 | Fecht et al. . |
| 4,877,031 | 10/1989 | Conway et al. ..................... 604/96 |
| 4,892,519 | 1/1990 | Songer et al. ...................... 606/194 |
| 4,909,252 | 3/1990 | Goldberger . |
| 4,932,413 | 6/1990 | Shockey et al. . |
| 4,950,239 | 8/1990 | Gahara et al. . |
| 4,960,411 | 10/1990 | Buchbinder . |

(List continued on next page.)

FOREIGN PATENT DOCUMENTS

| | | |
|---|---|---|
| 214721 | 3/1987 | European Pat. Off. . |
| 344530 | 12/1989 | European Pat. Off. . |
| 8303766 | 11/1983 | WIPO . |
| 8800071 | 1/1988 | WIPO . |
| 8803817 | 6/1988 | WIPO . |

OTHER PUBLICATIONS

Abstract of WO89/03701, Harmjanz, D., May 5, 1989.
King et al., *Coronary Arterioigraphy and Angioplasty*, McGraw-Hill Book Co., pp. 399–460.

(List continued on next page.)

*Primary Examiner*—C. Fred Rosenbaum
*Assistant Examiner*—Corrine Maglione
*Attorney, Agent, or Firm*—Knobbe, Martens, Olson & Bear

[57] ABSTRACT

Dilatation catheters for use in administering treatments to relieve stenotic regions within a body lumen while maintaining blood flow past the dilatation balloons are described. According to the present invention, perfusion ports are provided in both a guidewire lumen and in a bypass lumen in several alternative embodiments in order to provide increased blood flow past the dilatation balloon.

12 Claims, 4 Drawing Sheets

U.S. PATENT DOCUMENTS

| | | |
|---|---|---|
| 4,976,690 | 12/1990 | Solar et al. . |
| 4,983,167 | 1/1991 | Sahota . |
| 4,988,356 | 1/1991 | Crittenden et al. . |
| 5,000,734 | 3/1991 | Boussignac et al. ............ 604/96 |
| 5,000,743 | 3/1991 | Patel . |
| 5,002,531 | 3/1991 | Bonzel . |
| 5,019,042 | 5/1991 | Sahota . |
| 5,046,503 | 9/1991 | Schneiderman ............ 606/194 |
| 5,071,406 | 12/1991 | Jang . |
| 5,087,247 | 2/1992 | Horn et al. ............ 606/194 |
| 5,090,958 | 2/1992 | Sahota ............ 606/192 |
| 5,090,960 | 2/1992 | Don Michael ............ 604/96 |
| 5,137,513 | 8/1992 | McInnes et al. ............ 604/96 |
| 5,147,377 | 9/1992 | Sahota . |
| 5,160,321 | 11/1992 | Sahota ............ 604/96 |
| 5,169,395 | 12/1992 | Narciso . |

OTHER PUBLICATIONS

Simpson et al., "A New Catheter System for Coronary Angioplasty", *The American Journal of Cardiology*, vol. 49, Apr. 1, 1982, pp. 1216–1222.

Dorros, M. D. et al., "Probe TM, A Balloon Wire: Initial Experience", *Catheterization and Cardiovascular Diagnosis*, vol. 14, pp. 286–288, 1988.

*Steerable Balloon Dilatation Systems,* ©C. R. Bard, Inc., 1982.

"USCI Gruntzig TM Femoral, Iliac and Gruntzig Dilaca TM Renal Dilatation Catheters", C. R. Bard, Inc., 1980.

USCI ® "Safety Spring Guides", ©C. R. Bard, Inc., 1979.

"Gruntzig Dilaca TM Coronary Balloon Dilatation Catheters", ©C. R. Bard, Inc., 1982.

"USCI ® Probing Catheter".

"USCI Positrol II ® Nycore TM Cardiovascular Catheters", ©C. R. Bard, Inc., 1980.

"USCI Gruntzig Dilaca TM Coronary Dilatation Equipment", ©C. R. Bard, Inc., 1982.

"USCI Gruntzig Dilaca TM Coronary Dilatation Equipment", ©C. R. Bard, Inc., 1981.

"The Simpson–Robert TM Vascular Dilatation System for Percutaneous Transluminal Coronary Angioplasty (PTCA)", Advanced Catheter Systems, Inc.

"Cordis Infusion Catheter Set, A Simple, Reliable System for Thrombolysis of Coronary and Other Arteries", ©Cordis Corporation, 1982.

"Balloon Dilatation for Congenital Pulmonary Valve Stenosis", *Cardiology Product News*, p. 3, Jan. 1983.

M. G. Bourassa, M. D., *Bourassa Cardiovascular Catheters Sterile*, USCI 1972.

C. R. Bard, Inc., v. Advanced Cardiovascular Systems, Inc. Case No. 89–1719 decided Aug. 2, 1990.

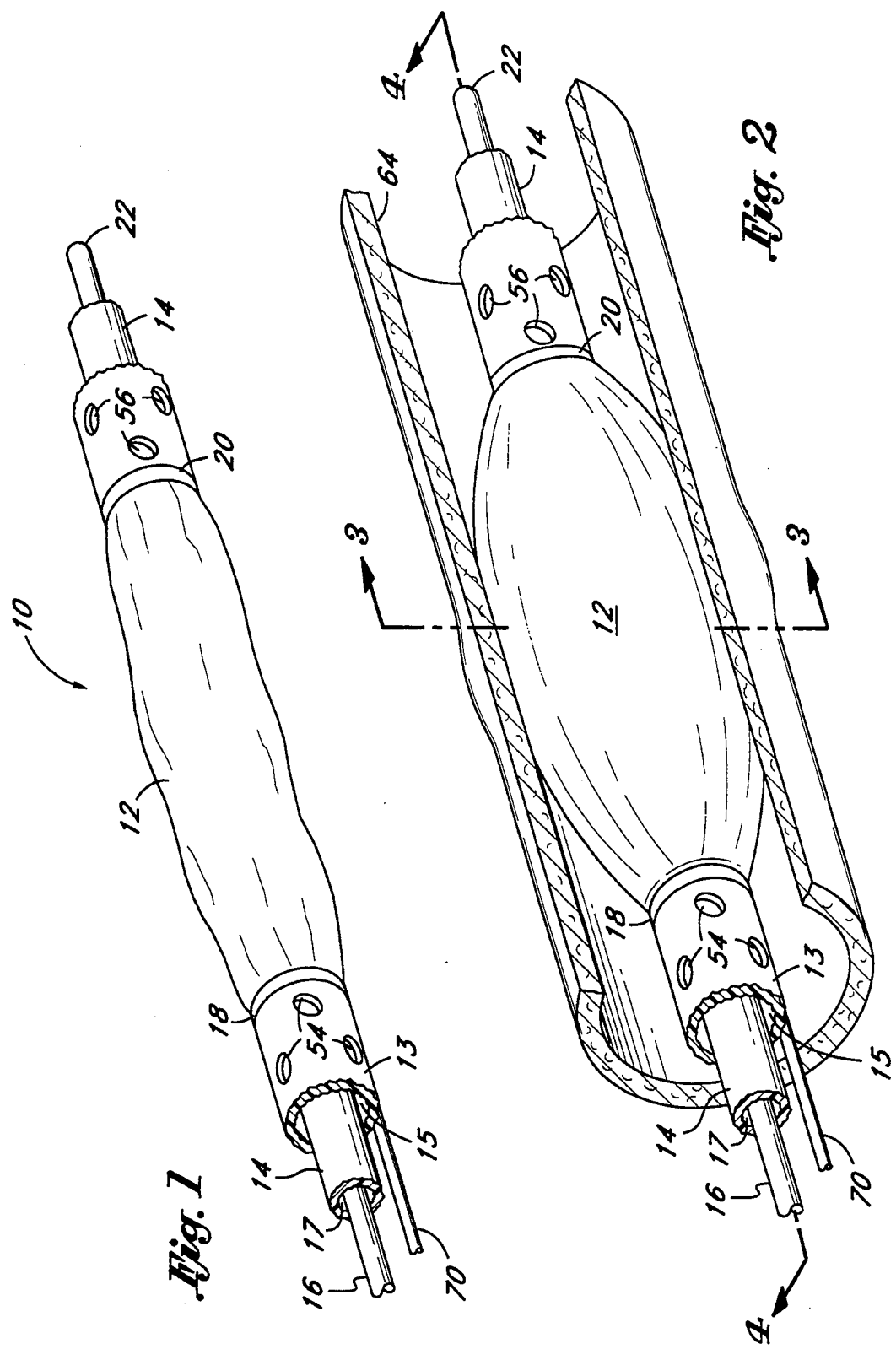

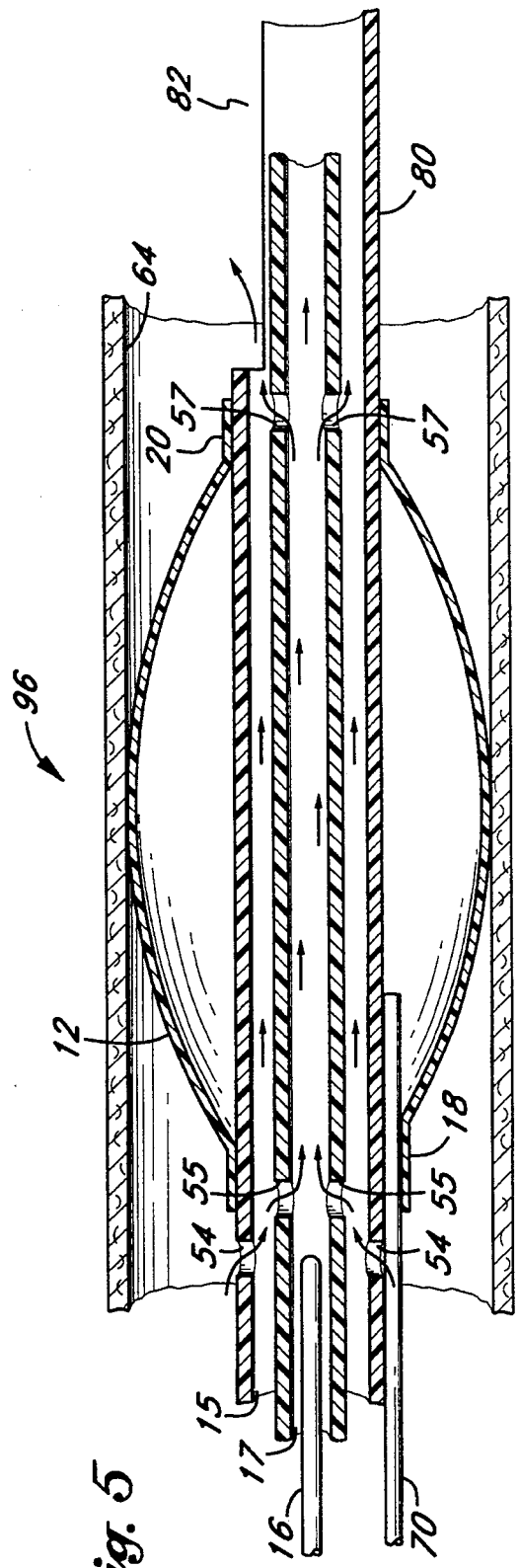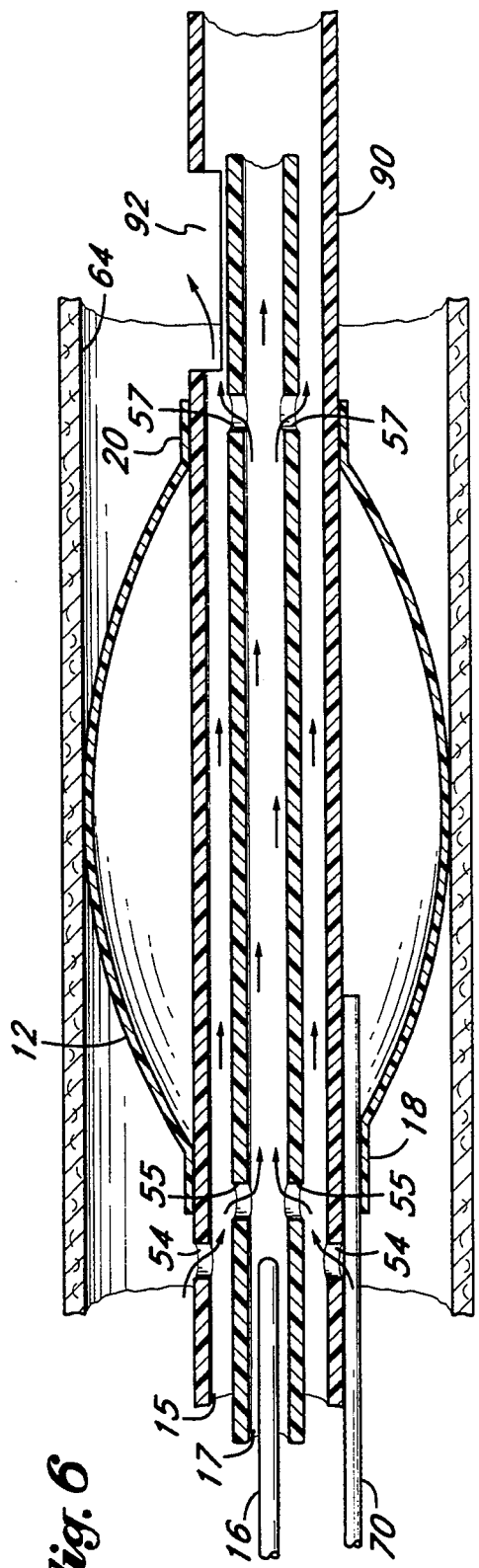

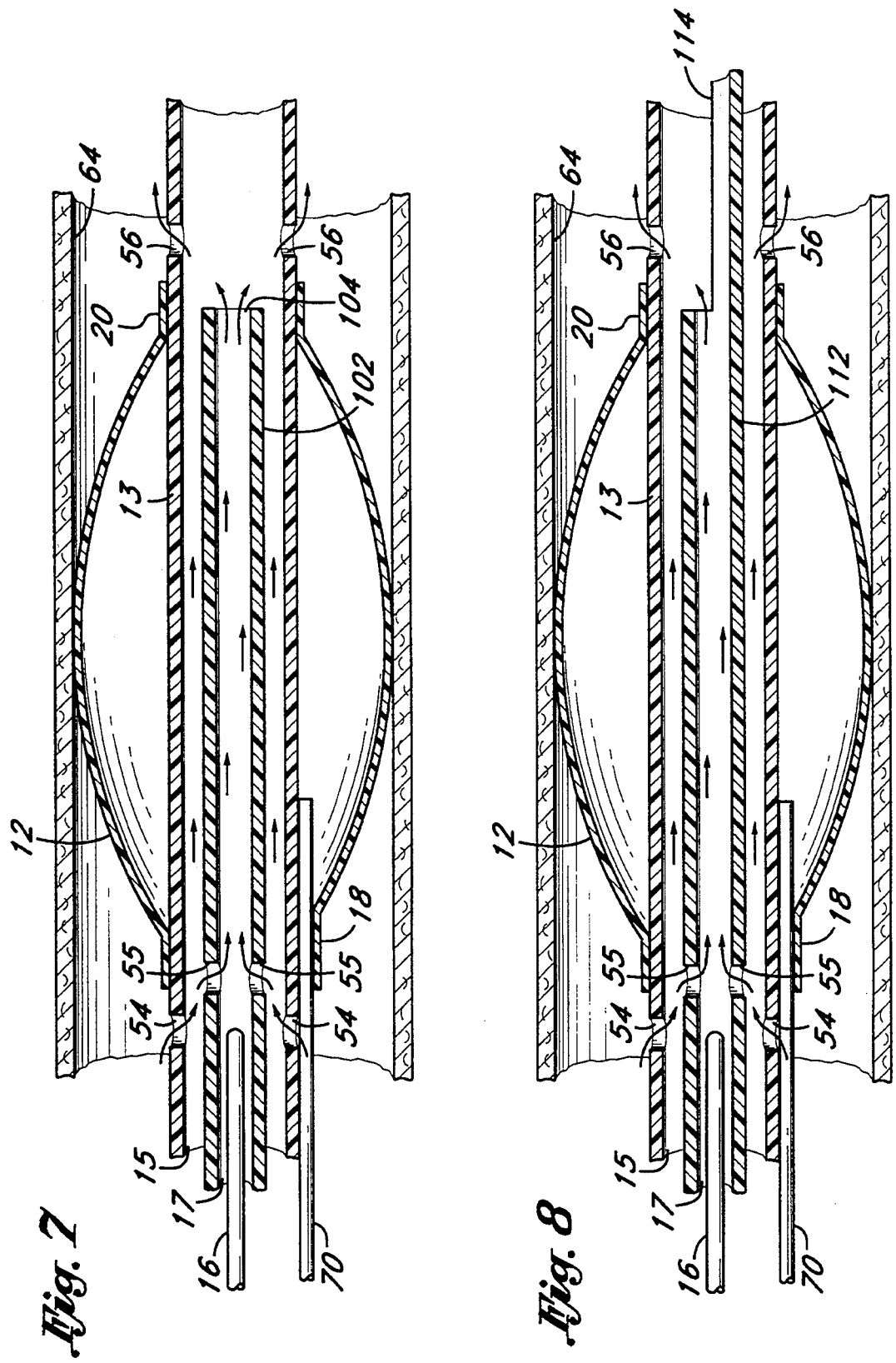

BLOOD PERFUSION BALLOON CATHETER

BACKGROUND OF THE INVENTION

1. Field of the Invention

The present invention relates generally to the field of catheters. More specifically, the present invention relates to dilatation catheters for use in administering treatments to relieve stenotic regions or to widen tubular passage, such as the coronary artery, as well as other vessels.

2. DESCRIPTION OF THE RELATED ART

A stenosis is a region of a blood vessel which has been narrowed to such a degree that blood flow is restricted. If the stenosis is sufficiently severe, treatment is required to restore adequate blood flow.

Percutaneous transluminal coronary angioplasty (PTCA), a procedure for treating a patient having a stenosis or constricted blood region in a coronary artery, has become a widely accepted therapeutic alternative to coronary arterial bypass surgery for many patients. PTCA increases the lumen by radial expansion. The main advantage of PTCA rests in the avoidance of the immediate post-operative discomforts associated with coronary bypass surgery, and certainly in the reduction of morbidity by use of this procedure.

Performing a coronary angioplasty involves inserting a balloon catheter into the desired coronary artery, locating the balloon at the arterial stenosis and injecting a suitable fluid into tile balloon to expand the balloon, and therefore the stenosis, radially outwardly. Some balloon catheters are too flexible for direct insertion into the patient's coronary artery. Accordingly, the standard angioplasty process begins with the insertion of a guiding catheter, or sleeve into the obstructed vessel, under local anesthesia. To facilitate the introduction of the guiding catheter, and to avoid damage to the body lumen at the puncture site, a guidewire is typically used in the insertion of the guiding catheter. The guiding catheter is designed to provide a conduit through which a balloon catheter is passed.

A lesion may be approached with a guidewire by advancing the catheter and guidewire as a unit, or by advancing the guidewire first. Steering the tip of the wire is done by the surgeon or by an assistant.

Ordinary balloon catheters have a balloon fastened around the exterior of a hollow catheter tube or catheter shaft. A thin tube provides a means for connecting the balloon to a suitable fluid supply for inflating the balloon.

A continuing problem with balloon dilatation catheters is the occlusion or reduction of blood flow while the balloon is expanded in an artery. Prior balloon dilatation catheters that allow blood to flow past the balloon to the distal portion of the artery are known and described in U.S. Pat. Nos. 4,581,017, 5,090,958, and 5,160,321, all issued to Harvinder Sahota, the present applicant. Each of these patents provides an apparatus for the perfusion of blood past the dilatation balloon. As catheter shaft sizes decrease, a continued need arises to maximize the flow of blood past the balloon.

SUMMARY OF THE INVENTION

The dilatation catheters of the present invention provide increased blood flow past the dilatation balloon. Several configurations of perfusion catheters for improved blood flow past the balloon are described herein.

One aspect of the present invention involves a dilatation catheter for relieving an obstructed coronary artery while maintaining a steady flow of blood past the obstruction. The catheter has an axially elongate catheter shaft with a guidewire conduit in the catheter shaft. The guidewire conduit defines a guidewire lumen. The catheter also has a dilatation balloon having a proximal end and a distal end secured to the catheter shaft. An inflation lumen is provided in the catheter shaft for transmitting pressurized fluid into and out of the dilatation balloon for selective inflation and deflation thereof. A perfusion lumen defined within the catheter shaft provides a path through which blood may bypass the dilatation balloon when the balloon is in an inflated state and occluding the artery. The perfusion lumen is separate from the guidewire lumen. A plurality of catheter shaft influent perfusion ports are disposed proximate to the proximal end of the dilatation balloon with the catheter shaft influent perfusion ports opening into the perfusion lumen so as to enable blood from the artery to enter the perfusion lumen. At least one catheter shaft effluent perfusion port is disposed proximate to the distal end of the dilatation balloon and opens into the perfusion lumen so as to conduct blood from the perfusion lumen back into the artery to maintain a steady flow of blood past the dilatation balloon during the dilatation process. A plurality of guidewire conduit influent perfusion ports are disposed proximate to the plurality of catheter shaft influent perfusion ports. The guidewire conduit influent perfusion ports open into the guidewire lumen so as to enable blood from the perfusion lumen to enter the guidewire lumen. Finally, at least one guidewire conduit effluent perfusion port is disposed proximate to the at least one catheter shaft effluent perfusion port and opens from the guidewire lumen into the perfusion lumen so as to conduct blood from the guidewire lumen back into the perfusion conduit.

Another aspect of the present invention involves a dilatation catheter for relieving an obstructed artery while maintaining a steady flow of blood past the obstruction. The catheter has an elongate tubular body with a dilatation balloon secured to the tubular body. The balloon has proximal and distal ends. A first conduit for receiving a guidewire extends axially through at least a portion of the elongate tubular body. A second conduit extends axially through at least a portion of the tubular body for allowing blood flow to bypass the dilatation balloon. At least one second conduit influent perfusion port is disposed upstream from the dilatation balloon and is in fluid communication with the second conduit so as to enable blood from the artery to enter the second conduit. At least one first conduit influent perfusion port is disposed proximate to the at least one second conduit influent perfusion port and is in fluid communication with the first conduit so as to enable blood from the second conduit to enter the first conduit. At least one second conduit effluent perfusion port is disposed downstream from the dilatation balloon and is in fluid communication with the second conduit so as to conduct blood from the second conduit back into the artery and maintain a steady blood flow past the dilatation balloon during the dilatation process. At least one first conduit effluent perfusion port is disposed proximate to the second conduit effluent perfusion port and is in fluid communication with the first conduit so as to conduct blood from the first conduit back into the second conduit.

In one embodiment, the at least one first conduit effluent perfusion port comprises an open end of the guidewire conduit with the open end being axially proximate to the distal end of the dilatation balloon.

In one embodiment, the at least one first conduit effluent perfusion port comprises a cutout in a distal end of the first conduit. In addition, the at least one first conduit effluent perfusion port may comprise a plurality of perfusion ports at the distal end of the guidewire conduit.

In a further embodiment, the second conduit effluent perfusion port comprises a cutout extending from an axial location proximate to the distal end of the dilatation balloon and extending distally for at least a portion along a distal portion of the catheter shaft.

Still a further aspect of the present invention involves a method of relieving stenotic regions of a body lumen while maintaining a steady flow of blood distal to the stenotic region. During the method, a guidewire is positioned within a body lumen, and an axially elongate dilatation catheter with a separate perfusion conduit and guidewire conduit is mounted on the guidewire by positioning the guidewire within the guidewire conduit. The dilatation catheter is then advanced along the guidewire into the body lumen so as to position a dilatation balloon proximate to the stenosis. A suitable pressurized fluid is injected into the dilatation balloon to increase radially the size of the dilatation balloon so as to increase the size of the body lumen by radial expansion. According to the present invention, blood channels through the perfusion conduit and through the guidewire conduit so as to bypass the dilatation balloon. After the procedure, the dilatation balloon is deflated, and the dilatation catheter is withdrawn from the body lumen.

Further objects, features and other advantages of the present invention will become apparent from the ensuing detailed description, when considered together with the appended drawings.

BRIEF DESCRIPTION OF THE DRAWINGS

FIG. 1 is a perspective view of a dilatation catheter having a guidewire with a separate guidewire lumen;

FIG. 2 is a view of a dilatation catheter, within a patient's artery, having a plurality of perfusion ports for allowing the continuous passage of blood flow through the artery while the balloon is inflated;

FIG. 5 is a cross-sectional view of a first alternative embodiment of the present invention;

FIG. 6 is a cross-sectional view of a second alternative embodiment of the present invention;

FIG. 7 is a cross-sectional view of a third alternative embodiment of the present invention; and FIG. 8 is a cross-sectional view of a fourth alternative embodiment of the present invention.

DETAILED DESCRIPTION OF THE PREFERRED EMBODIMENT

Figure 3:
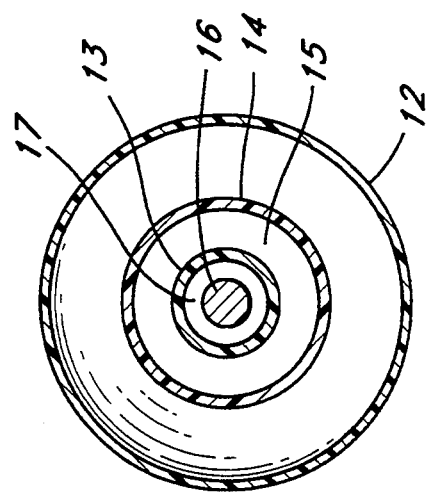
FIG. 3 is a cross-sectional view, taken along line 3—3 of FIG. 2, illustrating the several lumen within the catheter.

FIG. 1 illustrates a balloon dilatation catheter 10 embodying the present invention. The catheter 10 comprises a dilatation balloon 12, having a proximal end 18 and a distal end 20. The balloon 12 is fastened around an axially elongate catheter shaft 13. Preferably, a guidewire conduit 14 is positioned within the catheter shaft 13. The catheter shaft 13 provides a perfusion or bypass lumen 15 to allow blood flow to bypass the dilatation balloon 12. A guidewire 16 can be positioned within a guidewire lumen 17 defined within the guidewire conduit 14. In the present embodiment, the dilatation balloon 12 is attached such that the guidewire 16 is free to move within a guidewire lumen 17. Preferably, the guidewire 16 extends the length of the catheter 10, and exhibits a small segment, referred to as an advance wire 22, which extends beyond the distal end 20 of the dilatation balloon 12. Advantageously, the advance wire 22 may be of any suitable length, and may be preformed to any desired configuration to facilitate insertion of the catheter 10 and passage through the body lumen, as well-known in the art.

The proximal end 18 of the dilatation balloon 12 tapers to a diameter which approaches that of the catheter shaft 13. Preferably, the balloon 12 and catheter shaft 13 of the catheter 10 are made of a non-distensible material so that the balloon 12 can only be inflated to expand to the constructed size, as well-known in the art. Further attempts to inflate such structures result in an increase in pressure, but no significant increase in diameter.

The dilatation catheter 10 illustrated in FIG. 1 is suited for use in distal arteries and for severe stenosis. In use, the catheter 10 is inserted into the body lumen until the dilatation balloon 12 is proximate the stenotic area. Following sometimes several inflations and deflations, the catheter 10 is withdrawn.

Figure 4:
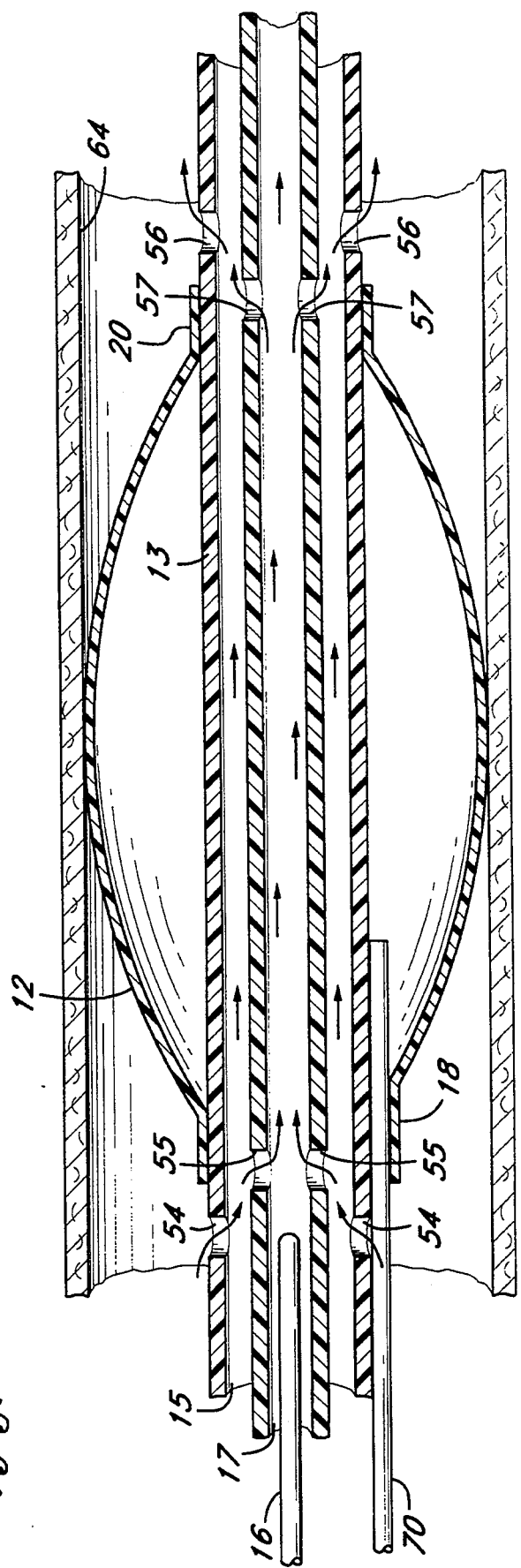
FIG. 4 is a cross-sectional view, taken along line 4—4 of FIG. 2, illustrating, by way of arrows, the perfusion of blood through the catheter.

FIGS. 2–4 further illustrate a first embodiment of the improved perfusion catheter of the present invention. The balloon catheter has a plurality of perfusion ports 54, 56 in the catheter shaft 13, positioned on opposite ends 18, 20 of the dilatation balloon 12. As illustrated in FIG. 2, when the balloon 12 is in an inflated state within an artery 64, it completely occludes blood flow past the arterial wall. The catheter shaft 13 defines the bypass lumen 15 (best seen in FIG. 3). The bypass lumen 15 is independent from the guidewire lumen 17 through which the guidewire 16 passes. The bypass lumen 15 allows blood to flow past the dilation balloon 12 so as to maintain blood flow to the distal side of the occluding balloon 12. The guidewire 16 need not be withdrawn in order to provide the passage for blood flow through the bypass lumen 15. This is significant in that withdrawal and reinsertion of the guidewire 16 can sometimes result in damage to the arterial wall 64.

The improved perfusion catheter of the present invention further includes, as depicted in FIG. 4, perfusion ports 55 and 57 at opposite ends 18, 20 of the dilatation balloon 12. The perfusion ports 55 and 57 are in the wall of the guidewire conduit 14 and open from the perfusion lumen 15 into the guidewire lumen 17. The perfusion ports 55 and 57 are provided to allow for increased blood flow past the dilatation balloon 12 when necessary. The guidewire 16 can be withdrawn from the guidewire lumen 17 to allow blood to enter influent perfusion ports 55 and exit effluent perfusion ports 57. By providing the holes in both the guidewire conduit 14 and in the catheter shaft 13, the dilatation catheter 10 provides increased blood flow past the balloon 12. All perfusion ports may be spaced around the catheter shaft 13 and guidewire conduit 14 to best allow blood to flow.

Not infrequently, it is determined that angioplasty will be unable to restore the blood flow rate to an acceptable level. In such a case, the patient is prepared for emergency bypass surgery. If the catheter is fully withdrawn from the affected vessel and the vessel becomes totally obstructed, infarction of the area distal to the obstruction will begin to occur. A guidewire left in place across the lesion will provide a small opening through which a small amount of blood may flow beyond the stenosis; however, this blood flow is not usually sufficient to prevent infarction. Advantageously, if the dilatation balloon 12 is left across the stenosis in a deflated state, blood will perfuse through the perfusion ports 54, 56 and the bypass lumen 15 to maintain a steady flow of blood distal to the obstruction. If the guidewire 16 is backed out far enough to allow blood to enter the influent perfusion ports 55 in the guidewire tube 14, increased blood flow is provided. Thus, the catheter 10 can effectively serve as a stent while preparing the patient for emergency bypass surgery.

FIG. 4 shows an axial cross section taken along line 4—4 of FIG. 2, but with the guidewire 16 backed out far enough such that blood can perfuse through the guidewire lumen 17. Arrows in the figure represent the flow of blood through the influent perfusion ports 54 of the catheter shaft 13 and through the influent perfusion ports 55 of the guidewire conduit 14, and out the effluent perfusion ports 57 of the guidewire conduit 14, and out the effluent perfusion ports 56 of the catheter shaft 13. FIG. 4 also depicts an inflation lumen 70 which is used to couple the balloon 12 to a suitable fluid supply for inflation, as well-known in the art.

FIG. 5 depicts, in cross section, a first alternative embodiment of an improved perfusion catheter 96 of the present invention. As shown in FIG. 5, the perfusion catheter has the dilatation balloon 12, the guidewire conduit 14 with influent perfusion ports 55 and effluent perfusion ports 57, and an alternative catheter shaft 80. The alternative catheter shaft 80 has influent perfusion ports 54, as in the previous embodiment, at the proximal end 18 of the dilatation balloon 12. At the distal end 20 of the dilatation balloon 12, the catheter shaft 80 has a slit or cutout 82 to more freely permit the flow of blood. In the embodiment of FIG. 5, the perfusion holes 55, 57 can be provided, or the guidewire tube 14 can be constructed without perfusion holes 55, 57. The administering physician can also leave the guidewire 16 in position or back the guidewire out for additional blood flow in the embodiment where the guidewire tube 14 has perfusion ports 55, 57. The catheter shaft 80 of the embodiment of FIG. 5 may also have effluent perfusion ports (not shown) in addition to the cutout 82, as in the previous embodiments. The cutout 82 of a portion of the catheter shaft 80 wall preferably extends to a distal end 83 of the catheter shaft 80 from a point near the distal end 20 of the dilatation balloon 12.

FIG. 6 illustrates a second alternative embodiment of an improved perfusion catheter of the present invention. The second alternative embodiment has the dilatation balloon 12, the guidewire conduit 14 with influent perfusion ports 55 and effluent perfusion ports 57 and a second alternative embodiment catheter shaft 90. In this second alternative embodiment, the catheter shaft 90 has a cutout 92 removed that does not extend to the complete distal end 93 of the catheter shaft 90. The catheter shaft 90 has the influent perfusion ports 54 at the proximal end 18 of the balloon 12, as in the previous embodiments, and may also have effluent perfusion ports (not shown) in addition to the cutout 92. As in the embodiment of FIG. 5, the guidewire conduit can be constructed with or without perfusion ports 55 and 57.

FIG. 7 depicts a third alternative embodiment of an improved dilatation catheter. The catheter has the dilatation balloon 12, the catheter shaft 13 with influent perfusion ports 54 and effluent perfusion ports 56. The catheter further has an alternative guidewire conduit 102 that ends approximately even with the axial location of the distal end 20 of the dilatation balloon 12. The guidewire tube 102 opens at a distal end 104 into the perfusion lumen 15. In this embodiment, if the guidewire 16 is backed out far enough, blood can enter the influent perfusion ports 54 into the perfusion lumen 15, and also can enter the influent perfusion ports 55 of guidewire conduit 102. The blood that enters the guidewire conduit 102, exits the guidewire conduit 102 at the open end 104, passes into the perfusion lumen 15, and exits the catheter through the effluent perfusion ports 56 of the perfusion lumen 15.

FIG. 8 depicts a fourth alternative embodiment of an improved dilatation catheter of the present invention. The fourth alternative embodiment has the dilatation balloon 12 having proximal and distal ends 18 and 20. The catheter shaft 13 has the perfusion lumen 15. The catheter has an alternative guidewire conduit 112. The perfusion lumen 15 has the influent perfusion ports 54 and effluent perfusion ports 56, as in the previous embodiments. The guidewire conduit 112 has influent perfusion ports 55, as in the previous embodiments, and has a cutout 114 starting at an axial location approximately even with the distal end 20 of the dilatation balloon 12 and extending for at least a portion of the guidewire conduit 112, and possibly to a distal end of the guidewire conduit 112, as depicted in FIG. 8. In addition, the guidewire conduit 112 may also be constructed with effluent perfusion ports (not shown) in the area of the cutout 114.

The improved dilatation catheters of FIGS. 1-8 provide for increased blood flow past a stenosis and past a dilatation balloon, which is particularly advantageous in modern dilatation catheters having small diameter catheter shafts.

It will be appreciated that certain structural variations are possible within the scope of the present invention. For instance, other alternative embodiments which increase the combined internal diameters of the lumens carrying blood past the dilatation balloon are envisioned within the present invention. The foregoing detailed description is to be clearly understood as given by way of illustration, the spirit and scope of this invention being defined by the appended claims.

What is claimed is:

1. A dilatation catheter for relieving an obstructed coronary artery while maintaining a steady flow of blood past the obstruction, comprising:
   an axially elongate catheter shaft,
   a dilatation balloon secured to said catheter shaft, said dilatation balloon having a proximal end and a distal end;
   a guidewire conduit in said catheter shaft, said guidewire conduit defining a guidewire lumen which traverses said dilatation balloon;
   an inflation lumen in fluid communication with said dilatation balloon;

a perfusion lumen defined by said catheter shaft for providing a path through which blood may bypass said dilatation balloon when said balloon is in an inflated state and occluding said artery, said perfusion lumen separate from said guidewire lumen;

a plurality of catheter shaft influent perfusion ports disposed proximate to the proximal end of said dilatation balloon, said influent ports opening into said perfusion lumen so as to enable blood from said artery to enter said perfusion lumen;

at least one catheter shaft effluent perfusion port opening into said perfusion lumen, said catheter shaft effluent perfusion port disposed distal to the distal end of said dilatation balloon so as to conduct blood from said perfusion lumen back into said artery and maintain a steady flow of blood past said dilatation balloon during the dilatation process;

a plurality of guidewire conduit influent perfusion ports disposed near to said plurality of catheter shaft influent perfusion ports, said guidewire conduit influent perfusion ports opening into said guidewire lumen to as to enable blood from said perfusion lumen to enter said guidewire lumen to traverse said dilatation balloon; and at least one guidewire conduit effluent perfusion port opening from said guidewire lumen into said perfusion lumen, said guidewire conduit effluent perfusion port disposed proximate to said at least one catheter shaft effluent perfusion port so as to conduct blood from said guidewire lumen back into said perfusion conduit.

2. A dilatation catheter for relieving an obstructed artery while maintaining a steady flow of blood past the obstruction, comprising:

an elongate tubular body;

a dilatation balloon secured to said tubular body, said balloon having proximal and distal ends;

an inflation lumen in fluid communication with said dilatation balloon;

a first conduit extending axially through at least a portion of said elongate tubular body for receiving a guidewire and extending through said dilatation balloon, said first conduit having a proximal end and a distal end;

a second conduit extending axially through at least a portion of the tubular body and extending through said dilatation balloon for allowing blood flow to bypass said dilatation balloon when said dilatation balloon is in an expanded state;

at least one second conduit influent perfusion port in fluid communication with said second conduit, said influent perfusion port disposed upstream from said dilatation balloon so as to enable blood from said artery to enter said second conduit;

at least one first conduit influent perfusion port in fluid communication with said first conduit, said first conduit influent perfusion port disposed near said at least one second conduit influent perfusion port so as to enable blood from said second conduit to enter said first conduit;

at least one second conduit effluent perfusion port in fluid communication with said second conduit, said second conduit effluent perfusion port disposed downstream from said dilatation balloon so as to conduct blood from said second conduit back into said artery and maintain a steady blood flow past said dilatation balloon during the dilatation process; and at least one first conduit effluent perfusion port in fluid communication with said first conduit, said first conduit effluent perfusion port disposed proximate said second conduit effluent perfusion port and configured so as to conduct blood from said first conduit back into said second conduit.

3. The dilatation catheter of claim 2, wherein said at least one first conduit effluent perfusion port comprises an open end of said guidewire conduit, said open end being axially near to said distal end of said dilatation balloon.

4. The catheter of claim 2, wherein said at least one first conduit effluent perfusion port comprises a cutout in said distal end of said first conduit.

5. The catheter of claim 2, wherein said at least one first conduit effluent perfusion port further comprises a plurality of perfusion ports at said distal end of said first conduit.

6. The catheter of claim 2, wherein said second conduit effluent perfusion port comprises a cutout extending from an axial locating near to said distal end of said dilatation balloon and extending distally for at least a portion of the catheter shaft along a distal portion of said catheter shaft.

7. A dilatation catheter for relieving an obstructed coronary artery while maintaining a steady flow of blood past the obstruction, comprising:

an axially elongate catheter shaft, said catheter shaft having a proximal end and a distal end;

a guidewire lumen in said catheter shaft;

a dilatation balloon secured to said catheter shaft;

an inflation lumen in fluid communication with said dilatation balloon;

a perfusion lumen defined by said catheter shaft for providing a path through which blood may bypass said dilatation balloon when said balloon is in an inflated state, said perfusion lumen separate from said guidewire lumen;

at least one catheter shaft influent perfusion port disposed proximal to said dilatation balloon, said at least one influent port opening into said perfusion lumen so as to enable blood from said artery to enter said perfusion lumen;

at least one catheter shaft effluent perfusion port in said perfusion lumen distal said dilatation balloon so as to enable blood from said perfusion lumen to enter the artery;

at least one guidewire lumen influent perfusion port disposed proximal to said dilatation balloon so as to enable blood from said perfusion lumen to enter said guidewire lumen; and at least one guidewire lumen effluent perfusion port distal said dilatation balloon so as to enable blood from said guidewire lumen to exit said guidewire lumen.

8. The dilatation catheter of claim 7, wherein said at least one guidewire lumen effluent perfusion port distal said dilatation balloon permits blood to exit said guidewire lumen and enter said perfusion lumen.

9. The dilatation catheter of claim 7, wherein said at least one guidewire lumen effluent perfusion port permits blood contained in said guidewire lumen to exit said guidewire lumen and enter the artery.

10. The dilatation catheter of claim 7, wherein said at least one catheter shaft influent perfusion port is proximate said at least one guidewire lumen influent perfusion port.

11. The dilatation catheter of claim 7, wherein said at least one catheter shaft effluent perfusion port is near said at least one guidewire lumen effluent perfusion port are proximate.

12. A method of relieving stenotic regions of a body lumen while maintaining a steady flow of blood distal to the stenotic region, said method comprising the steps of:

positioning a guidewire within a body lumen;

mounting an axially elongate dilatation catheter with a separate perfusion conduit and guidewire conduit on the guidewire by positioning the guidewire within the guidewire conduit;

advancing the dilatation catheter along the guidewire into the body lumen so as to position a dilatation balloon, attached to said axially elongate dilatation catheter, proximate said stenosis;

injecting a suitable pressurized fluid into said dilatation balloon via an inflation lumen to increase radially the size of said dilatation balloon so as to increase the size of said body lumen by radial expansion;

channelling blood through said perfusion conduit and through said guidewire conduit, both said perfusion conduit and said guidewire conduit traversing said dilatation balloon, so as to bypass said dilatation balloon;

deflating the dilatation balloon; and withdrawing said dilatation catheter from said body lumen.

* * * * *

UNITED STATES PATENT AND TRADEMARK OFFICE
CERTIFICATE OF CORRECTION

PATENT NO. : 5,370,617
DATED : December 6, 1994
INVENTOR(S) : Harvinder Sahota

It is certified that error appears in the above-indentified patent and that said Letters Patent is hereby corrected as shown below:

Column 7, line, 22 "lumen to as to" should be changed to read --lumen so as to--

Column 8, line, 21 "axial locating near" should be changed to read --axial location near--

Signed and Sealed this

Twenty-seventh Day of February, 1996

Attest:

BRUCE LEHMAN

*Attesting Officer*     *Commissioner of Patents and Trademarks*